(12) United States Patent
Hoium et al.

(10) Patent No.: US 7,610,091 B2
(45) Date of Patent: Oct. 27, 2009

(54) APPARATUS AND METHOD FOR DETECTING LEAD ADEQUACY AND QUALITY

(75) Inventors: Harold H. Hoium, Eden Prairie, MN (US); Stephen J. Ryan, Chaska, MN (US)

(73) Assignee: Harbinger Medical, Inc., Eden Prairie, MN (US)

( * ) Notice: Subject to any disclaimer, the term of this patent is extended or adjusted under 35 U.S.C. 154(b) by 299 days.

(21) Appl. No.: 11/600,355

(22) Filed: Nov. 16, 2006

(65) Prior Publication Data
US 2007/0093871 A1   Apr. 26, 2007

Related U.S. Application Data

(63) Continuation of application No. 09/957,657, filed on Sep. 20, 2001, now Pat. No. 7,171,265, and a continuation-in-part of application No. 09/487,557, filed on Jan. 19, 2000, now Pat. No. 6,445,947, and a continuation-in-part of application No. 09/126,864, filed on Jul. 31, 1998, now Pat. No. 6,129,678.

(60) Provisional application No. 60/234,054, filed on Sep. 20, 2000, provisional application No. 60/116,396, filed on Jan. 19, 1999, provisional application No. 60/133,983, filed on May 13, 1999.

(51) Int. Cl.
*A61N 1/18* (2006.01)

(52) U.S. Cl. .................. 607/27; 607/1; 607/2; 607/36; 607/37; 607/38; 607/115; 439/909

(58) Field of Classification Search ................. 607/1–2, 607/27, 36–38, 115–116; 600/515; 439/506, 439/909
See application file for complete search history.

(56) References Cited

U.S. PATENT DOCUMENTS

| | | | |
|---|---|---|---|
| 4,537,201 A | 8/1985 | Delle-Vedove et al. | |
| 4,552,150 A | 11/1985 | Zacouto | |
| 4,577,639 A | 3/1986 | Simon et al. | |
| 4,802,491 A | 2/1989 | Cohen et al. | |
| 5,109,862 A | 5/1992 | Kelen et al. | |
| 5,117,834 A | 6/1992 | Kroll et al. | |
| 5,178,154 A | 1/1993 | Ackmann et al. | |
| 5,188,116 A | 2/1993 | Pommrehn et al. | |

(Continued)

FOREIGN PATENT DOCUMENTS

GB    2301037    5/1996

*Primary Examiner*—Carl H Layno
*Assistant Examiner*—Deborah Malamud
(74) *Attorney, Agent, or Firm*—Patterson, Thuente, Skaar & Christensen, P.A.

(57) ABSTRACT

A system and method for detecting lead adequacy and quality is disclosed. The system includes leads attached to a package having known electrical or optical characteristics. The package is adapted to interface with a testing device that allows the operator to ascertain whether the leads are appropriate for the desired task. This allows the testing of the lead set without the need to remove it from the package. The system of the present invention generally includes packaging of known electrical or optical characteristics, a package testing interface, and a lead testing assembly including hardware and/or software to determine whether the leads in question fulfill the desired characteristics. The lead testing assembly may be freestanding or may be incorporated into an existing testing instrument.

3 Claims, 2 Drawing Sheets

U.S. PATENT DOCUMENTS

| | | |
|---|---|---|
| 5,191,524 A | 3/1993 | Pincus et al. |
| 5,215,099 A | 6/1993 | Haberl et al. |
| 5,269,313 A | 12/1993 | DePinto |
| 5,351,687 A | 10/1994 | Kroll et al. |
| 5,412,589 A | 5/1995 | Williams et al. |
| 5,431,692 A | 7/1995 | Hansen et al. |
| 5,437,285 A | 8/1995 | Verrier et al. |
| 5,555,888 A | 9/1996 | Brewer et al. |
| 5,555,889 A | 9/1996 | Karagueuzian et al. |
| 5,560,368 A | 10/1996 | Berger |
| 5,560,370 A | 10/1996 | Verrier et al. |
| 5,755,742 A * | 5/1998 | Schuelke et al. ............... 607/27 |
| 5,984,102 A * | 11/1999 | Tay ........................... 206/701 |
| 6,115,638 A | 9/2000 | Groenke |
| 6,129,678 A | 10/2000 | Ryan et al. |
| 6,141,585 A | 10/2000 | Prutchi et al. |

* cited by examiner

APPARATUS AND METHOD FOR DETECTING LEAD ADEQUACY AND QUALITY

RELATED APPLICATIONS

This application is a continuation of application Ser. No. 09/957,657 filed Sep. 20, 2001, now U.S. Pat. No. 7,171,265 which in turn claims the benefit of U.S. Provisional Application No. 60/234,054 filed Sep. 20, 2000 and which is a Continuation-In-Part of co-pending U.S. patent application Ser. No. 09/487,557, Jan. 19, 2000, now U.S. Pat. No. 6,445,947, which in turn claims priority under 35 U.S.C. § 119(e), to previously filed U.S. Provisional Applications No. 60/116,396, filed Jan. 19, 1999; and U.S. Provisional Application No. 60/133,983, filed May 13, 1999, and which is also a Continuation-in Part of co-pending U.S. patent application Ser. No. 09/126,864, filed Jul. 31, 1998, now U.S. Patent 6,129,678, the subject matter of which are all incorporated herein by reference.

FIELD OF INVENTION

The present invention relates to medical testing devices utilizing or measuring electromagnetic radiation. More particularly, the present invention relates to a method and apparatus for ascertaining that the leads utilized in testing are the intended lead for the task, of the intended quality, an acceptable alternative lead, or an acceptable alternative quality of lead for particular medical testing scenarios.

BACKGROUND OF THE INVENTION

A wide variety of modern medical testing instruments utilize leads to either sense electromagnetic energy or to deliver electromagnetic energy for testing or for therapeutic reasons.

A variety of different medical testing regimens utilize test leads for sensing or receiving electromagnetic energy emanating from the human body. For example, electrocardiogram testing (EKG or ECG) senses electrical impulses associated with the beating of the heart. Electroencephalogram testing (EEG) senses electrical activity related to brain function. Electromyelogram testing (EMG) senses electrical activity related to the functioning of skeletal muscle.

These instruments often are utilized to sense extremely low power levels emanating from the living organisms such as the human body. Because of the low energy levels involved, small variations in the electrical characteristics of the electrical leads can create significant differences in results.

In general, the leads used with these instruments are used for tests that are acute in nature. That is, the leads are applied to the test subject for a relatively short period of time. The leads are not intended for long-term use. An example of long-term use would be the leads that are implanted with an implantable cardioverter/defibrillator or pacemaker. The leads involved there are required to be more robust than the leads in question here. In addition, since those leads are associated with expensive devices and surgical procedures and lead expense is relatively trivial in the scope of the entire operation cost is not a great concern.

Therefore, lead sets utilized with these acute testing and treatment instruments are often disposable in nature. They are intended for use only once and are then intended to be discarded. Because of this disposable nature the market for leads for acute use is more price sensitive than that for chronic leads. Nonetheless it is essential for accurate diagnosis and treatment that acute use leads be within the desired range of electrical parameter tolerances.

In addition, some medical testing instrumentation senses electromagnetic radiation in the ultraviolet, visible light or infrared wavelengths. For example, certain intracardiac catheters contain fiber optic leads that sense reflected light radiation from structures in the heart. In this application, the applicant will primarily refer to leads. It should be understood that for the purposes of this application the term 'lead' also includes fiber optic strands. The invention is equally applicable to leads using fiber optic strands to transmit light energy.

Because sensing leads may be used to detect extremely low power levels, minor damage or deterioration may create significant loss of sensitivity and thus alteration of testing results. Handling the leads more than necessary may accelerate damage to them.

Various leads are used in medical testing to stimulate biological activity. For example, certain types of cardiac testing provide stimulation to the heart in addition to sensing EKG activity. An example of such testing is disclosed in U.S. Pat. No. 6,129,678 to Ryan and Hoium. This application is incorporated herein in its entirety by this reference.

Lead sets can also be used to deliver electromagnetic energy for therapeutic reasons. For example, intracardiac catheters often are utilized to deliver energy for purposes of ablating tissue. Such electromagnetic energy may be delivered, for example, in the form of radio frequency energy or laser light energy.

Often, multi-purpose lead sets may be utilized. Multi-purpose lead sets may contain electrical leads for sensing, electrical leads for stimulating, electrical leads for therapeutic purposes, fiber optic leads for sensing or therapeutic purposes, or any combination thereof.

With the proliferation of leads used for medical testing purposes, a variety of problems arise. First, any type of lead set will suffer degradation of performance with use. In use, leads may be exposed to variations in temperature, bodily fluids, skin oils, atmospheric oxygen and high oxygen environments. Any of these factors will tend to lead to corrosion of metal parts of the lead as well as loss of the lead's insulator dielectric strength. For example, skin surface leads have primary attributes of impedance, inductance and capacitance. Over time, and with exposure to environmental factors, these qualities of skin surface leads can change. If these qualities change sufficiently, electrical impulses transmitted by use of the skin surface leads are altered. Thus, the data measured will be changed causing instrument readings to be imprecise, potentially leading to an erroneous diagnosis.

Additionally, certain types of medical testing leads may suffer degradation of their electrical or optical qualities over a period of storage. Again, corrosion, loss of dielectric strength or other deterioration may affect the electrical qualities of leads while in storage.

The proliferation of leads also creates a variety of potential problems created by the use of the wrong leads for a given circumstance. Multipurpose instrumentation may require different types of leads for different testing or treatment scenarios.

Lead sets may be very similar in appearance and, if reusable, once removed from their packaging may be difficult to identify. The use of the wrong set of leads for a given testing procedure may lead to degraded or altered data results and potentially erroneous diagnosis. In addition, leads used for stimulation or therapeutic purposes may not deliver the appropriate level of stimulating or therapeutic electromagnetic energy. This can result in over treatment or under treatment of the medical condition in question.

Under some circumstances there may be a need to perform medical testing when the desired lead set is unavailable. Under these circumstances it would be desirable to be able to determine whether an alternative lead set would provide acceptable results. In some circumstances instrumentation may be calibrated to a particular lead set to increase the precision of the result.

Many types of lead sets are provided in disposable configurations intended for a single use and then immediately discarded. With the increasing pressure to hold down costs there can be a temptation to reuse lead sets that are intended for only a single use. This activity increases the risk of erroneous diagnosis and also potentially increases the risk of infection if the lead set is intended to be sterile at its initial use. It would be desirable to be able to determine whether a lead set had previously been used and to prevent the reuse of lead sets that are intended for a single disposable use.

Thus, it would be desirable in the field of medical testing arts to be able to readily test leads prior to use, even prior to opening the packaging, to determine whether those leads have deteriorated in storage, to ascertain that they are the appropriate leads for the test or that they are an acceptable alternative set. In addition, it would be desirable to determine whether reusable leads have degraded from the rigors of use prior to their application. It would be further desirable to identify and/or disable reuse of single use leads so that they could not be reused beyond their desired intent.

SUMMARY OF THE INVENTION

The present invention solves many of the problems indicated above. The invention provides leads attached to a package having known electrical or optical characteristics. The package is adapted to interface with a testing device that allows the operator to ascertain whether the leads are appropriate for the desired task.

The system of the present invention generally includes packaging of known electrical or optical characteristics, a package testing interface, and a lead testing assembly including hardware and/or software to determine whether the leads in question fulfill the desired characteristics. The lead testing assembly may be freestanding or may be incorporated into an existing testing instrument.

Leads generally include an electrode or a connector for attaching to an electrode. For the purposes of this application the end of the lead that interfaces with the patient will be referred to as a lead termination. This term is intended to encompass electrodes, connectors to electrodes, catheters, fiber optic emitters or receivers and any other lead end that is distal from a patient testing instrument.

The lead terminations are releasably secured to the packaging so that they are in electrical or optical communication with the packaging. The packaging is connectable to the package testing interface thus creating an electrical or optical communication to the testing instrument. This allows the leads to be evaluated to ascertain whether the leads are appropriate for the desired task without the need to open the packaging. In the case of sterile leads this preserves the sterility of the leads. The verification of leads is simplified since it is not necessary to remove the leads from the packaging for testing.

Further, since the leads are protected by the package during testing and handling, sensitive leads may be tested numerous times without damage. Also, the interface allows for multiple connections and disconnections to the package without creating stress or wear on the lead terminations themselves, further protecting the integrity of the leads.

Isolation of the lead terminations in their connection to the packaging allows for testing of leads that operate at very low power levels without interference with one another.

DETAILED DESCRIPTION OF THE INVENTION

Figure 1:
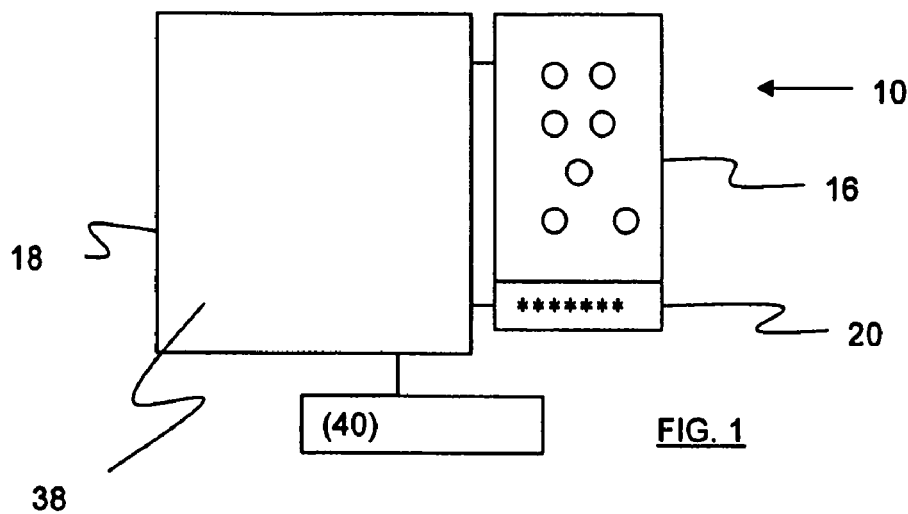
FIG. 1 is a schematic block diagram of the apparatus for detecting lead adequacy and quality in accordance with the present invention.
Figure 2:
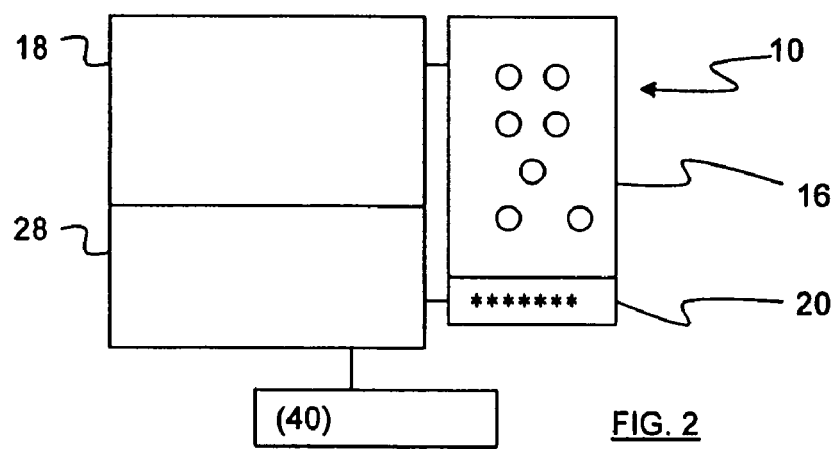
FIG. 2 is an alternative embodiment of the apparatus for detecting lead adequacy and quality in accordance with the present invention.
Figure 3:
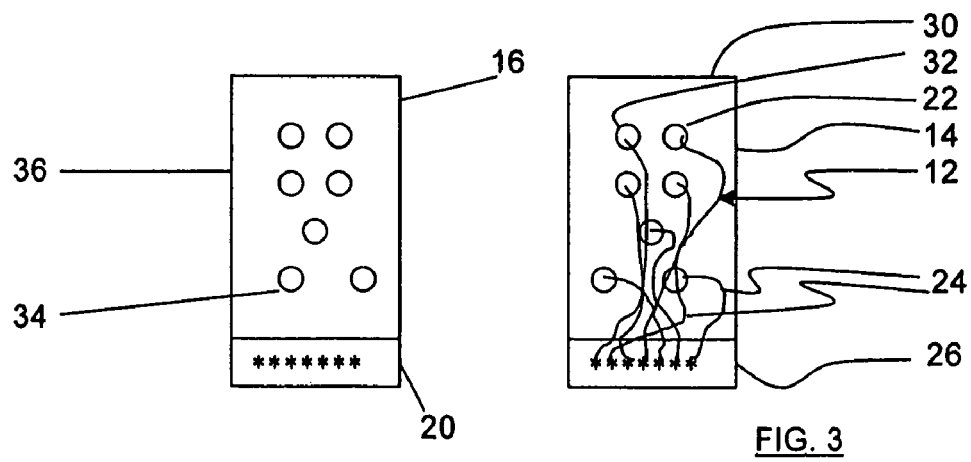
FIG. 3 is a schematic diagram of the lead package and package interface in accordance with the present invention.
Figure 4:
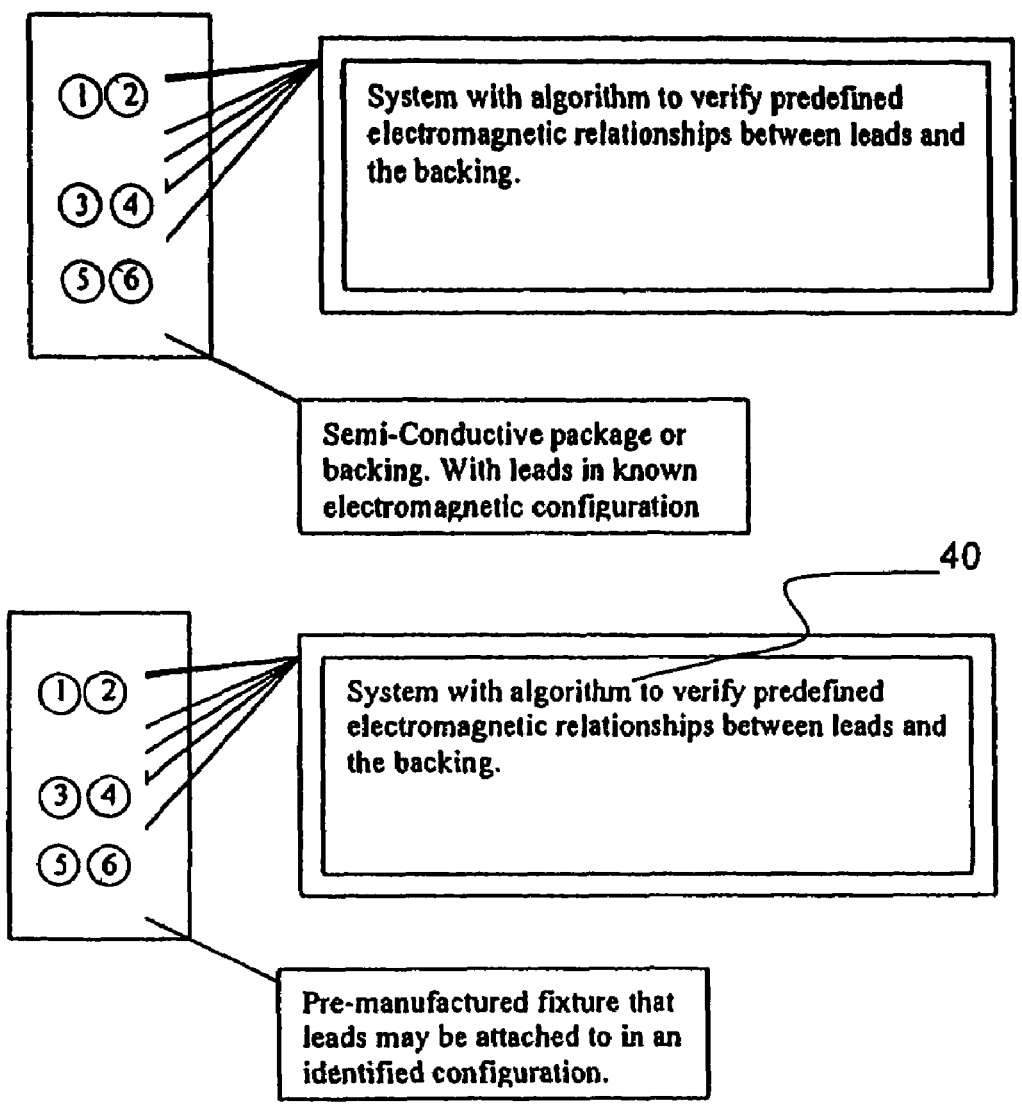
FIG. 4 is a schematic of the lead package, interface and algorithm in accordance with the present invention.

Referring to FIGS. 1 and 3, an apparatus 10 for detecting lead adequacy and quality in accordance with the present invention generally includes leads 12 enclosed in package 14, testing interface 16, testing subassembly 18 and connector interface 20.

Leads 12 may be any conventional testing, therapeutic or ablating leads. Leads 12 typically include a plurality of lead terminations 22, lead conductors 24 and connector 26. Lead conductors 24 may include electrical wires, other electrical conductors, or fiber optic wires for carrying electromagnetic radiation in the form of light (including visible light, infrared light and ultraviolet light.) Connector 26 is adapted to receive lead conductors 24 and to connect them to an appropriate testing instrument 28. Connector 26 includes appropriate electrical and/or optical connecting members.

Leads 12 may be used to sense or deliver signals that are electrical, magnetic or light energy related in character. Some examples of instruments where this apparatus and method may be employed are ECG, signal averaged ECG, external pacemakers, external defibrillators, EP pacing systems, pacing catheters, defibrillation catheters, RF ablation catheters, optical ablation catheters, implantable pacemakers, implantable defibrillators, Holter monitors, external neurological stimulators, internal neurological stimulators, EEG, EMG, external neuromuscular stimulators, internal neuromuscular stimulators, TENS and TNS. This list is exemplary and is not intended to be exhaustive.

Package 14 includes backing 30 which further includes an isolated lead pad 32 for each individual lead termination 22. Each isolated lead pad 32 is adapted to releasably receive lead termination 22. The mechanical connection between isolated lead pad 32 and lead termination 22 may be made by adhesives, clips, screws, clamps or any other means of connecting lead terminations or electrodes known to those skilled in the art. The electromagnetic connection between isolated lead pad 32 and lead termination 22 is adapted for the particular type of application. For example, isolated lead pad 32 provides an electrical contact for electrical leads, an inductive interface for magnetic leads or an optical transmission interface for fiber optic leads.

Testing interface 16 includes a plurality of lead pad connectors 24 and a package engaging member 36. Testing subassembly 18 is interposed between testing interface 16 and connector interface 20. Testing subassembly 18 includes electronic components 38 and software algorithms 40.

Connector interface 20 is adapted to receive connector 26 and to attach each of leads 12, whether they be electrical or optical in nature, to testing subassembly 18.

Isolated lead pads 32 are configured to accept any of a variety of lead terminations and electrodes. Lead terminations include adhesive electrodes, screw attachments, pad electrodes, tines and helices. Any other type of lead termination is contemplated as being utilized with the present invention. For example, isolated lead pads 32 for use with an adhesive pad type electrode may be simple conductive plates of known electrical qualities. Isolated lead pads 32 for use with screw type electrodes may be a threaded bore adapted to receive the screw type electrode. Isolated lead pads 32 may be configured to receive optical leads, such as when associated with a laser ablation catheter. In this case, isolated lead pads 32 include a transmission medium of known optical qualities and an engagement member to releasably hold the catheter tip in contact with the transmission medium. Those skilled in the art will be able to create isolated lead pads of known electrical, magnetic or optical qualities for the myriad lead terminations that are used in the medical arts.

In another embodiment of the invention, isolated lead pads 32 are configured to distort, deform, tear or otherwise display an indication that the leads have been removed from the package. Removal of the leads may also create some change in the known electrical, magnetic or optical characteristics of isolated lead pads 32.

In operation, lead connector 26 is connected to connector interface 20 and package 14 is connected to package engaging member 36. Because package 14 includes isolated lead pads 32 the connection of package 14 to package engaging member 36 creates an electrical circuit in the case of electrical leads. In the case of optical or magnetic leads, an appropriate circuit is created as well. Each isolated lead pad 32 comes into contact with an associated corresponding lead pad connector 34. Because isolated lead pads 32 are of a known electrical magnetic or optical quality, electronic components 38 in combination with algorithm 40 are able to test the leads 12 while still in the package 14. The end result of this operation is that the quality and adequacy of leads 12 for a given purpose can be determined without the necessity of opening the package thus ensuring accurate testing for delivery of energy for a given medical situation.

In another embodiment of the invention, isolated lead pads 32 will indicate whether the leads have been removed from the package previously. This indication, whether it be due to distortion, deformation, tearing or some other indication that the leads have been removed from the package serves to warn the operator that the leads are intended for a single use and having been once used should not be used again.

In another embodiment of the invention, the characteristics of isolated lead pads 32 will be altered by the removal of leads 12. Therefore, when the package 14 is connected to package engaging member 36, the electronic components of the system for detecting lead quality and adequacy 10 will display an indication that the leads have been previously used and are no longer acceptable for use.

In operation, package 14 is engaged to testing interface 16. Engaging package 14 to testing interface 16 connects connector 26 to connector interface 20 and connects isolated lead pads 32 each to a corresponding lead pad connector 34.

Note that package 14 can be connected to testing interface 16 and connector interface 20 without placing significant stress on lead conductors 24, lead terminations 22 or connector 26. Connector 26 is a relatively robust component. Thus, connector 26 is well adapted to be connected and disconnected repeatedly. Lead conductors 24 and lead terminations 22 are relatively more subject to damage and wear. Since connection is limited to isolated lead pads 32, the more delicate components of lead 12 are protected from harm. This allows for the repeated testing and verification of leads 12 if need be.

In an additional embodiment of the invention, when leads 12 are removed from package 14, they are separated from backing 30. Backing 30 is altered by the removal of leads 12. This alteration both signals that the leads 12 have been previously used and prevents the repackaging and retesting of leads 12. This effectively prevents the intentional or inadvertent reuse of leads 12 that are intended for a single disposable use.

The written description filed as U.S. Provisional Patent Application No. 60/234,054 is attached as appendix A and is hereby incorporated by reference and made part of this application.

The present invention may be embodied in other specific forms without departing from the spirit of any of the essential attributes thereof; therefore, the illustrated embodiment should be considered in all respects as illustrative and not restrictive, reference being made to the appended claims rather than to the forgoing description to indicate the scope of the invention.

The invention claimed is:

1. A package for enclosing a lead set, the lead set optimized to induce Wedensky phenomena by sub-threshold transcutaneous stimulation for acute, short term use external to a body with a medical device that senses or delivers electromagnetic energy, the lead set comprising a connector, a plurality of leads and a plurality of lead terminations each lead termination being associated with one of the plurality of leads, the package comprising:

a fixture for supporting the lead terminations and the connector in a fixed geometric configuration relative to one another such that the fixture is engagable to a package interface operably coupled to a testing apparatus such that the lead set is in electromagnetic communication with the package interface via the connector and the lead terminations and the lead terminations are each releasably connected to an electromagnetically isolated lead pad interposed between the lead termination and the package interface, thereby facilitating the testing of the lead set for conformance with known desired electromagnetic characteristics;

in which the electromagnetically isolated lead pads are fixated in space relative to one another in a remanufactured fixture and the connector is releasably fixated in space relative to the electromagnetically isolated lead pads in the premanufactured fixture; and in which the fixture is altered by the removal of the leads such that the known electromagnetic transmission characteristics of the electromagnetically isolated lead pads are altered in a way that is identifiable by the testing apparatus thereby enabling the testing apparatus to deny reuse of the lead set.

2. The package as claimed in claim 1, in which the electromagnetic characteristics tested are selected from a group consisting of: impedance, inductance, capacitance, electrical spectral range or a combination thereof.

3. The package as claimed in claim 1, in which the fixture is altered by removal of the leads such that the leads cannot be reattached.

* * * * *